(12) United States Patent
Hoeffer et al.

(10) Patent No.: US 7,816,485 B2
(45) Date of Patent: Oct. 19, 2010

(54) CATALYZED PREPARATION OF (METH)ACRYLATES OF N-HYDROXYALKYLATED AMIDES

(75) Inventors: Frank Hoeffer, Bad Duerkheim (DE); Dietmar Haering, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 279 days.

(21) Appl. No.: 11/169,763

(22) Filed: Jun. 30, 2005

(65) Prior Publication Data

US 2006/0036063 A1 Feb. 16, 2006

Related U.S. Application Data

(60) Provisional application No. 60/679,665, filed on May 11, 2005.

(30) Foreign Application Priority Data

Jul. 29, 2004 (DE) .................. 10 2004 036 930

(51) Int. Cl.
*C08G 73/00* (2006.01)
(52) U.S. Cl. ............... 528/367; 548/324.1; 548/313.4; 528/361
(58) Field of Classification Search ............ 548/324.1, 548/313.4; 528/367
See application file for complete search history.

(56) References Cited

U.S. PATENT DOCUMENTS

| 2,871,223 | A | | 1/1959 | Hankins et al. |
| 4,777,265 | A | | 10/1988 | Merger et al. |
| 6,515,138 | B2 | * | 2/2003 | Weir et al. ............... 548/324.1 |
| 2006/0084779 | A1 | * | 4/2006 | Dietsche et al. ............. 528/272 |

FOREIGN PATENT DOCUMENTS

| EP | 0 236 994 A1 | | 9/1987 |
| EP | 0 263 749 A1 | | 4/1988 |
| EP | 0 999 229 A1 | | 5/2000 |
| JP | 62-175448 | * | 8/1987 |
| JP | 62-185059 | * | 8/1987 |
| JP | 62-230755 | * | 10/1987 |
| WO | WO2004/050888 | * | 6/2004 |
| WO | WO 2004/050888 A1 | | 6/2004 |

OTHER PUBLICATIONS

Regina Derango, et al., "The Lipase-Catalyzed Synthesis of Carbamoyloxyethyl Methacrylate", Biotechnology Letters, vol. 16, No. 3, Mar. 1994, pp. 241-246.

Joachim Probst, et al., "Homo-und Copolymerisation von N, N-disubstitulerten Carbamoyloxyalkytacrylaten und-methacrylaten", Makromol. Chem, 177, XP-009026952, 1976, pp. 2681-2695.

* cited by examiner

*Primary Examiner*—James Seidleck
*Assistant Examiner*—Gregory Listvoyb
(74) *Attorney, Agent, or Firm*—Oblon, Spivak, McClelland, Maier & Neustadt, L.L.P.

(57) ABSTRACT

Process for catalytically preparing (meth)acrylates of N-hydroxyalkylated amides and use thereof.

9 Claims, No Drawings

CATALYZED PREPARATION OF (METH)ACRYLATES OF N-HYDROXYALKYLATED AMIDES

The present invention relates to a process for catalytically preparing (meth)acrylates of N-hydroxyalkylated amides and to the use thereof.

(Meth)acrylic esters are prepared usually by catalytical esterification of (meth)acrylic acid or transesterification of other (meth)acrylic esters with alcohols in the presence of strong acids or strong bases. It is generally therefore often impossible to selectively prepare acid- or base-sensitive (meth)acrylic esters by an esterification or transesterification.

Ureido alcohols in the context of the present document are those compounds which have at least one N—(C=O)—N— group and at least one hydroxyl group (—OH). Analogously, N-hydroxyalkylated amides in the context of the present document are those compounds which have at least one $Z^1$-(C=O)—N— group and at least one hydroxyl group (—OH), in which the hydroxyl group is joined to the nitrogen atom of the $Z^1$-(C=O)—N— group and $Z^1$ is defined as listed below.

Such ureido alcohols and N-hydroxyalkylated amides hydrolyze extremely readily under the influence of acid or base. In addition, particularly in the case of the reaction with base in the presence of (meth)acrylate, side reactions, for example in a Michael addition, are to be expected; see, for example, EP-A1 236 994, page 3, line 47 ff.

EP-A1 236 994 describes the preparation of ureido (meth) acrylates by transesterifying (meth)acrylate in the presence of titanium alkoxides or 1,3-dicarbonyl chelates of titanium, zirconium, iron or zinc.

A disadvantage of these compounds is that the metal compounds are moisture-sensitive and are therefore deactivated readily. In addition, traces of the catalysts which remain in the product influence any polymerization which follows, and therefore have to be removed from the product in a costly and inconvenient manner. Such a removal is usually carried out by means of an aqueous scrubbing, so that the product subsequently has to be dried.

JP-A 62-185 059 and JP-A 62-175 448 describe the reaction of (meth)acrylates with alkylamino alcohols in the presence of alkali metal carbonates. JP-A 62-230 755 describes the reaction of (meth)acrylates with alkylamino alcohols in the presence of alkali metal phosphates.

The disclosure is restricted to alkyl- and dialkylamino alcohols and does not comprise any information on ureido alcohols or N-hydroxyalkylated amides.

U.S. Pat. No. 2,871,223 discloses the preparation of ureido (meth)acrylates by reaction of ureido alcohols with (meth) acryloyl chloride.

The use of (meth)acryloyl chloride in the reactions described leads to salt formation and, owing to its high reactivity, to unselective reactions, for example diacrylations.

The preparation of (meth)acrylic esters by an enzymatic esterification or transesterification is generally known, for example from EP 0 999 229 A1.

In *Biotechnol. Lett.* 1994, 16, 241-246, Derango et al. describe the lipase-catalyzed preparation of carbamoyloxy-ethyl methacrylate by transesterifying 2-hydroxyethyl carbamate with vinyl methacrylate. A full conversion is achieved as a result of the specific vinyl methacrylate reactant, since released vinyl alcohol is removed from the reaction equilibrium as acetaldehyde. A disadvantage of this process is that vinyl methacrylate is not commercially available. In addition, O-hydroxyalkylated carbamoyls are involved and thus constitute a different reaction system than the ureido alcohols and N-hydroxyalkylated amides treated here.

In WO 2004/50888, further O-hydroxyalkylated carbamoyls are esterified or transesterified enzymatically with (meth)acrylic acid/esters. Here too, a different reaction system is involved than the ureido alcohols and N-hydroxyalkylated amides treated here.

It is an object of the present invention to provide a further process, by which (meth)acrylates of N-hydroxyalkylated amides can be prepared from simple reactants in high conversions and high purities. The synthesis should proceed under mild conditions, so that products result which have a low color number and high purity. In particular, the content of poly(meth)acrylated products should be suppressed. Any catalyst needed should also be easily removable and not result in any further aftertreatments, for example in the form of workup steps, of the reaction product.

The object is achieved by a process for preparing (meth) acrylates of N-hydroxyalkylated amides, in which cyclic N-hydroxyalkylated amides (C)

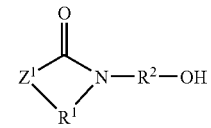

or open-chain N-hydroxyalkylated amides (O)

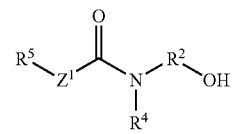

where $Z^1$ is oxygen, sulfur, unsubstituted or substituted phosphorus or un- or monosubstituted nitrogen (N—$R^3$), $R^1$ and $R^2$ are each independently $C_2$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —$[X_i]_k$—H, $R^3$, $R^4$ and $R^5$ are each independently hydrogen, $C_1$-$C_{18}$-alkyl, or $C_2$-$C_{18}$-alkyl, $C_2$-$C_{18}$-alkenyl, $C_6$-$C_{12}$-aryl, $C_5$-$C_{12}$-cycloalkyl which are each optionally interrupted by one or more oxygen and/or sulfur atoms and/or one or more substituted or unsubstituted imino groups, or a five- to six-membered heterocycle having oxygen, nitrogen and/or sulfur atoms, where the radicals mentioned may each be substituted by aryl, alkyl, aryloxy, alkyloxy, heteroatoms and/or heterocycles, and $R^3$ and $R^5$ may also together form a five- to twelve-membered ring, with the proviso that, in the case that $Z^1$=O, $R^5$ is only unsubstituted $C_1$-$C_{18}$-alkyl, $C_6$-$C_{12}$-aryl or $C_5$-$C_{12}$-cycloalkyl, k is a number from 1 to 50 and $X_i$ for each i=1 to k may independently be selected from the group of —$CH_2$—$CH_2$—O—, —$CH_2$—$CH_2$—N(H)—, —CH₂—CH₂—CH₂—N(H)—, —CH₂—CH(NH₂)—, —CH₂—CH(NHCHO)—, —CH₂—CH(CH₃)—O—, —CH(CH₃)—CH₂—O—, —CH₂—C(CH₃)₂—O—, —C(CH₃)₂—CH₂—O—, —CH₂—CH₂—CH₂—O—, —CH₂—CH₂—CH₂—CH₂—O—, —CH₂—CHVin—O—, —CHVin-CH₂—O—, —CH₂—CHPh—O— and —CHPh—CH₂—O— where Ph is phenyl and Vin is vinyl, are esterified with (meth)acrylic acid or transesterified with at least one (meth)acrylic ester (D) in the presence of at least one heterogeneous catalyst selected from the group consisting of inorganic salts (S) and enzymes (E).

With the aid of the process according to the invention, it is possible to prepare (meth)acrylates of N-hydroxyalkylated amides in high yield, under mild conditions, with good color numbers and without washing steps for purifying products.

In this document, (meth)acrylic acid represents methacrylic acid and acrylic acid, preferably methacrylic acid.

In the above definitions, $C_2$-$C_{20}$-alkylene optionally substituted by aryl, alkyl, aryloxy, alkyloxy, heteroatoms and/or heterocycles is, for example, 1,2-ethylene, 1,2-propylene, 1,3-propylene, 1,4-butylene, 1,6-hexylene, 2-methyl-1,3-propylene, 2-ethyl-1,3-propylene, 2,2-dimethyl-1,3-propylene, 2,2-dimethyl-1,4-butylene, $C_5$-$C_{12}$-cycloalkylene optionally substituted by aryl, alkyl, aryloxy, alkyloxy, heteroatoms and/or heterocycles is, for example, cyclopropylene, cyclopentylene, cyclohexylene, cyclooctylene, cyclododecylene, $C_2$-$C_{20}$-alkylene optionally substituted by aryl, alkyl, aryloxy, alkyloxy, heteroatoms and/or heterocycles and interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups is, for example, 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3-enylene, 1-oxa-1,5-pent-3-ynylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1,7-heptylene, 4-aza-1-oxa-1,6-hexylene, 1-aza4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1,7-dioxa-4-(2'-hydroxyethyl)-1,7-heptylene, 4-aza-1-oxa-(2'-hydroxyethyl)-1,6-hexylene or 1,4-piperazinylene, $C_6$-$C_{12}$-arylene optionally substituted by aryl, alkyl, aryloxy, alkyloxy, heteroatoms and/or heterocycles is, for example, 1,2-, 1,3- or 1,4-phenylene, 4,4'-biphenylene, tolylene or xylylene, $C_1$-$C_{18}$-alkyl, or $C_2$-$C_{18}$-alkyl optionally interrupted by one or more oxygen and/or sulfur atoms and/or one or more substituted or unsubstituted imino groups, is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)-ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di-(methoxycarbonyl)-ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_2$-$C_{18}$-alkenyl optionally interrupted by one or more oxygen and/or sulfur atoms and/or one or more substituted or unsubstituted imino groups is, for example, vinyl, 1-propenyl, allyl, methallyl, 1,1-dimethylallyl, 2-butenyl, 2-hexenyl, octenyl, undecenyl, dodecenyl, octadecenyl, 2-phenylvinyl, 2-methoxyvinyl, 2-ethoxyvinyl, 2-methoxyallyl, 3-methoxyallyl, 2-ethoxyallyl, 3-ethoxyallyl or 1- or 2-chlorovinyl, $C_6$-$C_{12}$-aryl optionally interrupted by one or more oxygen and/or sulfur atoms and/or one or more substituted or unsubstituted imino groups is, for example, phenyl, tolyl, xylyl, α-naphthyl, β-naphthyl, 4-diphenyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl optionally interrupted by one or more oxygen and/or sulfur atoms and/or one or more substituted or unsubstituted imino groups is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, or else a saturated or unsaturated bicyclic system, for example norbornyl or norbornenyl, and five- to six-membered heterocycle having oxygen, nitrogen and/or sulfur atoms and optionally interrupted by one or more oxygen and/or sulfur atoms and/or one or more substituted or unsubstituted imino groups is, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

Examples of $R^1$ are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2- dimethyl-1,3-propylene and 2,2-dimethyl-1,4-butylene, 1,2-cyclopentylene, 1,3-cyclopentylene, 1,2-cyclohexylene, 1,3-cyclohexylene and ortho-phenylene; preference is given to 1,2-ethylene, 1,2-propylene, 1,3-propylene, particular preference to 1,2-ethylene and 1,2-propylene and very particular preference to 1,2-ethylene.

Examples of $R^2$ are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 1,2-cyclopentylene, 1,3-cyclopentylene, 1,2-cyclohexylene, 1,3-cyclohexylene and ortho-phenylene; preference is given to 1,2-ethylene, 1,2-propylene, 1,3-propylene, particular preference to 1,2-ethylene and 1,2-propylene and very particular preference to 1,2-ethylene.

Examples of $R^3$ and $R^5$ are each independently hydrogen or $C_1$-$C_4$-alkyl, which in this document represents methyl, ethyl, isopropyl, n-propyl, n-butyl, isobutyl, sec-butyl or tert-butyl, preferably hydrogen, methyl, ethyl, n-propyl and n-butyl, more preferably hydrogen, methyl, ethyl and n-butyl and even more preferably hydrogen, methyl and ethyl and in particular hydrogen.

When $R^3$ and $R^5$ form a combined ring, $R^3$ and $R^5$ together may be 1,4-butylene, 1,5-pentylene or 3-oxa-1,5-pentylene.

Examples of $R^4$ are hydrogen, methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, naphthyl or benzyl.

$Z^1$ is preferably O or $NR^3$, more preferably $NR^3$.

Preference is given to the cyclic alcohols (C) over the open-chain alcohols (O).

Preferred individuals (C) are 2'-hydroxyethylethyleneurea, 3'-hydroxypropylethyleneurea, 2'-hydroxypropylethyleneurea, 2'-hydroxyethyl-1,3-propyleneurea, 2'-hydroxypropyl-1,3-propyleneurea, 3'-hydroxypropyl-1,3-propyleneurea, 2'-hydroxyethyl-1,2-propyleneurea, 2'-hydroxypropyl-1,2-propyleneurea, 3'-hydroxypropyl-1,2-propyleneurea, 1-(2'-hydroxyethyl)imidazolidine-2,4-dione, 1-(2'-hydroxyethyl)dihydropyrimidine-2,4-dione or 3-(2-hydroxyethyl)oxazolidin-2-one. Particular preference is given to 2'-hydroxyethylethyleneurea, 3'-hydroxypropylethyleneurea, 2'-hydroxyethyl-1,3-propyleneurea and 3'-hydroxypropyl-1,3-propyleneurea.

Preferred individuals (O) are N-(2-hydroxyethyl)urea, N-(2-hydroxypropyl)urea, N-(3-hydroxypropyl)urea, N',N'-dimethyl-N-(2-hydroxyethyl)urea, N',N'-dimethyl-N-(2-hydroxypropyl)urea, N',N'-dimethyl-N-(3-hydroxypropyl) urea, N',N'-diethyl-N-(2-hydroxyethyl)urea, N',N'-diethyl-N-(2-hydroxypropyl)urea, N',N'-diethyl-N-(3-hydroxypropyl)urea, N',N'-di-n-butyl-N-(2-hydroxyethyl) urea, N',N'-di-n-butyl-N-(2-hydroxypropyl)urea and N',N'-di-n-butyl-N-(3-hydroxypropyl)urea; particular preference is given to N-(2-hydroxyethyl)urea, N-(2-hydroxypropyl)urea and N-(3-hydroxypropyl)urea.

In step c), the esterification with (meth)acrylic acid or preferably the transesterification of the alcohol (C) or (O) with at least one, preferably one (meth)acrylate (D), is effected in the presence of at least one heterogeneous catalyst selected from the group consisting of inorganic salts (S) and enzymes (E).

Compounds (D) may be (meth)acrylic acid or esters of (meth)acrylic acid with a saturated alcohol, preferably saturated $C_1$-$C_{10}$-alkyl esters of (meth)acrylic acid, more preferably saturated $C_1$-$C_4$-alkyl esters of (meth)acrylic acid.

In the context of this document, saturated means compounds without C—C multiple bonds (apart of course from the C=C double bond in the (meth)acrylic units).

Examples of compounds (D) are methyl, ethyl, n-butyl, isobutyl, tert-butyl, n-octyl and 2-ethylhexyl (meth)acrylate, 1,2-ethylene glycol di- and mono(meth)acrylate, 1,4-butanediol di- and mono(meth)acrylate, 1,6-hexanediol di- and mono(meth)acrylate, trimethylolpropane tri(meth)acrylate and pentaerythritol tetra(meth)acrylate.

Particular preference is given to methyl, ethyl, n-butyl and 2-ethylhexyl (meth)acrylate, very particular preference to methyl, ethyl and n-butyl (meth)acrylate, in particular to methyl and ethyl (meth)acrylate and especially to methyl (meth)acrylate.

The inorganic salts (S) which can be used in accordance with the invention are those which have a $pK_B$ of not more than 7.0, preferably of not more than 6.1 and more preferably of not more than 4.0. At the same time, the $pK_B$ should not be below 1.0, preferably not less than 1.5 and more preferably not less than 1.6.

In the context of this document, heterogeneous catalysts in accordance with the invention are those which have solubility in the reaction medium at 25° C. of not more than 1 g/l, preferably of not more than 0.5 g/l and more preferably of not more than 0.25 g/l.

The inorganic salt preferably has at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($R^6$—$COO^-$) where $R^6$ is $C_1$-$C_{18}$-alkyl, or $C_2$-$C_{18}$-alkyl or $C_6$-$C_{12}$-aryl which are each optionally interrupted by one or more oxygen and/or sulfur atoms and/or one or more substituted or unsubstituted imino groups.

Preference is given to carbonate and phosphate, particular preference to phosphate.

Phosphate also includes the condensation products, for example diphosphates, triphosphates and polyphosphates.

The inorganic salt preferably has at least one cation selected from the group consisting of alkali metals, alkaline earth metals, ammonium, cerium, iron, manganese, chromium, molybdenum, cobalt, nickel and zinc.

Preference is given to alkali metals and particular preference to lithium, sodium or potassium.

Particularly preferred inorganic salts are $Li_3PO_4$, $K_3PO_4$, $Na_3PO_4$, $K_2CO_3$ and $Na_2CO_3$ and hydrates thereof; very particular preference is given to $K_3PO_4$.

According to the invention, $K_3PO_4$ may be used in anhydrous form or else as the tri-, hepta- or nonahydrate.

The esterification or transesterification catalyzed by an inorganic salt is effected generally at from 50 to 140° C., preferably at from 50 to 100° C., more preferably at from 60 to 90° C. and most preferably at from 60 to 80° C.

If appropriate, the reaction may be carried out under slightly reduced pressure or, for example, from 300 hPa to atmospheric pressure when the water released in the esterification or the low-boiling alcohol formed in the transesterification, if appropriate as an azeotrope, is to be distilled off.

The molar ratio between (meth)acrylic acid or (meth) acrylic ester and alcohol (C) or (D) in the esterification or transesterification catalyzed by an inorganic salt is generally 2-6:1 mol/mol, preferably 2-3.5:1 mol/mol and more preferably 2.5-3.0:1 mol/mol.

The reaction time in the esterification or transesterification catalyzed by an inorganic salt is generally from 30 min to 24 hours, preferably from 45 min to 18 hours, more preferably from 3 to 12 hours and most preferably from 5 to 10 hours.

The content of inorganic salts in the reaction medium is generally in the range of from about 0.01 to 5 mol %, preferably 0.1-1.8 and more preferably 0.3-1.5 mol %, based on the sum of the components (C) and (O) used.

In the esterification or transesterification, polymerization inhibitors (see below) are necessarily required.

Preference is given to the presence of oxygenous gases (see below) during the reaction catalyzed by an inorganic salt.

In the esterification or transesterification catalyzed by an inorganic salt, the products are generally obtained with a color number below 500 APHA, preferably below 200 and more preferably below 150 (to DIN ISO 6271).

Enzymes (E) which can be used in accordance with the invention are, for example, selected from hydrolases (E.C. 3.-.-.-) and among these particularly among the esterases (E.C. 3.1.-.-), lipases (E.C. 3.1.1.3), glycosylases (E.C. 3.2.-.-) and proteases (E.C. 3.4.-.-), in free form or in chemically or physically immobilized form on a support, preferably lipases, esterases or proteases and more preferably esterases (E.C. 3.1.-.-). Very particular preference is given to Novozyme® 435 (lipase from *Candida antarctica* B) or lipase from *Alcaligenes* sp., *Aspergillus* sp., *Mucor* sp., *Penicilium* sp., *Geotricum* sp., *Rhizopus* sp., *Burkholderia* sp., *Candida* sp., *Pseudomonas* sp., *Thermomyces* sp. or porcine pancreas; special preference is given to lipase from *Candida antarctica* B or from *Burkholderia* sp.

The enzymatic esterification or transesterification with a (meth)acrylate is effected generally at from 20 to 100° C., preferably from 20 to 80° C., more preferably from 30 to 70° C., most preferably from 40 to 60° C.

The upper limit of the temperature is of course the boiling point of the solvent or of the alcohol released in a transesterification.

If appropriate, the reaction may be carried out under slightly reduced pressure of, for example, from 300 hPa to atmospheric pressure, when the water released in the esterification or the low-boiling alcohol formed in the transesterification, if appropriate as an azeotrope, is to be distilled off.

The enzyme content in the reaction medium is generally in the range from about 0.1 to 10% by weight, based on the sum of the components (C) or (O) and (D) used.

The molar ratio between (meth)acrylic acid or (meth)acrylic ester and alcohol (C) or (D) in the enzymatically catalyzed esterification or transesterification is generally 1-50: 1 mol/mol, preferably 5-20:1 mol/mol.

The reaction time in the enzymatically catalyzed esterification or transesterification is generally from 6 hours to 3 days, preferably from 8 hours to 2 days and more preferably from 12 to 24 hours.

Preference is given to adjusting the reaction time such that the conversion of all hydroxyl functions present in the alcohol is at least 70%, preferably at least 80%, more preferably at least 90%, even more preferably at least 95% and in particular at least 97%.

The enzymatically catalyzed reaction may optionally also be performed in the absence of stabilizers (see below); preference is given to performing it in the presence of at least one stabilizer.

The reaction products obtainable in the enzymatically catalyzed reaction generally have a color number of less than 100 APHA, preferably below 80 APHA.

The reaction parameters which follow apply, unless stated otherwise, both to the enzymatically catalyzed reaction and to the reaction catalyzed with inorganic salts.

The reaction may proceed in organic solvents or mixtures thereof or without addition of solvents. The mixtures are generally substantially anhydrous (i.e. water content below 10% by weight, preferably below 5% by weight, more preferably below 1% by weight and most preferably below 0.5% by weight). In addition, the mixtures are substantially free of primary and secondary alcohols, i.e. alcohol content below 10% by weight, preferably below 5% by weight, more preferably below 1% by weight and most preferably below 0.5% by weight.

Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, e.g. 1,2-dimethoxyethane, diethylene glycol dimethyl ether, polyethylene glycol dimethyl ether 500, $C_1$-$C_4$-alkylene carbonates, in particular propylene carbonate, $C_3$-$C_6$-alkylacetic esters, in particular tert-butylacetic esters, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and the mono- or polyphasic mixtures thereof.

In a particularly preferred embodiment of the transesterification, the reaction is carried out in the (meth)acrylic ester used as a reactant. Very particular preference is given to carrying out the reaction in such a way that the product (C) or (O) is obtained on completion of the reaction as an about 10-80% by weight solution in the (meth)acrylic ester used as the reactant, in particular as a from 20 to 50% by weight solution.

The reactants are either dissolved, suspended as solids or in an emulsion in the reaction medium. The initial concentration of the reactants is preferably in the range of from about 0.1 to 20 mol/l, in particular at from 0.15 to 10 mol/l or from 0.2 to 5 mol/l.

The reaction may be effected continuously, for example in a tubular reactor or in a stirred reactor battery, or batchwise.

The reaction may be carried out in all reactors suitable for such a reaction. Such reactors are known to those skilled in the art. Preference is given to effecting the reaction in a stirred tank reactor or a fixed bed reactor.

To mix the reaction mixture, any methods may be used. Special stirring apparatus is not required. The mixing may be effected, for example, by feeding in a gas, preferably an oxygenous gas (see below). The reaction medium may be mono- or polyphasic and the reactants are dissolved, suspended or emulsified therein, if appropriate initially charged together with the molecular sieve and admixed with the enzyme preparation at the start of the reaction, and also if appropriate once or more in the course of the reaction. The temperature is set to the desired value during the reaction and may, if desired, be increased or reduced during the course of the reaction.

When the reaction is carried out in a fixed bed reactor, the fixed bed reactor is preferably charged with immobilized enzymes, and the reaction mixture is pumped through a column filled with the enzyme. It is also possible to carry out the reaction in a fluidized bed, in which case the enzyme is used immobilized on a support. The reaction mixture may be pumped continuously through the column, and the flow rate can be used to control the residence time and thus the desired conversion. It is also possible to pump the reaction mixture in circulation through a column, in the course of which the alcohol released may also simultaneously be distilled off under reduced pressure.

The removal of water in the case of an esterification or alcohols which are released from the alkyl (meth)acrylates in a transesterification is effected continuously or stepwise in a manner known per se, for example by reduced pressure, azeotropic removal, stripping, absorption, pervaporation and diffusion through membranes or extraction.

The stripping may be effected, for example, by passing an oxygenous gas, preferably an air or air-nitrogen mixture, through the reaction mixture, if appropriate additionally to a distillation.

Suitable for the absorption are preferably molecular sieves or zeolites (pore size, for example in the range of about 3-10 angstrom), a removal by distillation or with the aid of suitable semipermeable membranes.

However, it is also possible to feed the removed mixture of alkyl (meth)acrylate and the parent alcohol thereof, which frequently forms an azeotrope, directly into a plant for preparing the alkyl (meth)acrylate, in order to reutilize it there in an esterification with (meth)acrylic acid.

It may be advantageous in the case of the enzymatically catalyzed reaction to remove water or alcohol released by means of a binary or ternary heteroazeotrope which boils very close to the temperature optimum of the enzyme used. The thus removed alcohol may then be removed by phase separation or membrane vapor separation.

On completion of the reaction, the reaction mixture obtainable from c) may be reused without further purification or it may, if required, be purified in a further step d).

In general, in step d) only the heterogeneous catalyst used is removed from the reaction mixture and the reaction product is removed from any organic solvent used.

A removal from the heterogeneous catalyst is effected generally by filtration, electrofiltration, absorption, centrifugation or decanting. The removed heterogeneous catalyst may subsequently be used for further reactions.

The removal from the organic solvent is effected generally by distillation, rectification or, in the case of solid reaction products, by filtration.

For the further purification of the reaction product, chromatography may also be carried out.

However, preference is given in step d) to removing only the heterogeneous catalyst and any solvent used.

The reaction conditions in the inventive, particularly in the enzymatic, esterification or transesterification are mild. Owing to the low temperatures and otherwise mild conditions, the formation of by-products in step c) is prevented, which could otherwise stem, for example, from chemical catalysts or as a result of undesired free-radical polymerization of the (meth)acrylate used, which can be prevented only by adding stabilizers. In the inventive reaction, the (meth) acrylic compound (D), over and above the storage stabilizer present in any case, may have added to it additional stabilizer in at least the (meth)acrylate used or in the reaction mixture, for example hydroquinone monomethyl ether, phenothiazine, phenols, for example 2-tert-butyl-4-methylphenol, 6-tert-butyl-2,4-dimethylphenol, or N-oxyls such as 4-hydroxy-2,2,6,6-tetramethylpiperidine N-oxyl, 4-oxo-2,2,6,6-tetramethylpiperidine N-oxyl or Uvinul® 4040P from BASF Aktiengesellschaft, for example in amounts of from 50 to 2000 ppm.

Advantageously, the esterification or transesterification is carried out in the presence of an oxygenous gas, preferably air or air-nitrogen mixtures.

The heterogeneous catalyst used in accordance with the invention may be removed from the end product without any problem; as a result of the solubility, low in accordance with the invention, of the heterogeneous catalyst in the reaction medium, at most insignificant traces of the catalyst remain in the product. As a result of this, the reaction product can generally be worked up by a simple filtration or decantation; costly and inconvenient scrubbings, neutralization and the like to remove the catalyst can be dispensed with by virtue of the process according to the invention.

The catalysts used in accordance with the invention exhibit a low tendency to side reactions. The inorganic salts are sufficiently basic to catalyze an esterification or transesterification but not too basic to catalyze side reactions, for example the Michael reaction mentioned at the outset, so that the process according to the invention can distinctly reduce the proportion of Michael adducts compared to the reactions known from the prior art.

In addition, the reaction is very selective under the inventive reaction conditions; in general, less than 10%, preferably less than 5%, of by-products (based on the conversion) are found.

Typical by-products of the reaction of the compounds (C) and (O) in which $Z^1$ is N—H with (meth)acrylic acid or (meth)acrylic esters are the (meth)acrylamide bonded via this nitrogen atom, the Michael adduct bonded via this nitrogen atom, the Michael adduct bonded via the free hydroxyl group, and products which result from an intra- or intermolecular elimination of the $R^5$-$Z^1$ group from the compounds (C) or (O), which can then in turn be esterified or transesterified.

A particular advantage of the inventive catalysts is that it was possible to suppress the proportion of multiply, i.e. at least doubly, (meth)acrylated products. Such products can only be removed with difficulty from the mono(meth)acrylated desired product. Since the desired product is to be used as a monomer or reactive diluent (see below), a content of multiply (meth)acrylated product is undesired, since such products lead to crosslinks which can increase the molecular weight of the products in polymerizations in an unforeseeable manner.

The (meth)acrylates, prepared in accordance with the invention, of N-hydroxyalkylated amides find use, for example, as monomers or comonomers in the preparation of dispersions, for example acrylic dispersions, as reactive diluents, for example in radiation-curable coating compositions, or in paints, preferably in exterior paints, and in dispersions for use in the paper sector.

The examples which follow are intended to illustrate the properties of the invention, but without restricting it.

EXAMPLES

"Parts" refer in this document, unless stated otherwise, to "parts by weight".

The apparatus consisted of a 500 ml four-neck round-bottom flask with air inlet tube, separating column, sampling point and internal temperature sensor. The apparatus was stirred with a magnetic stirrer at 300 rpm.

The separating column used was a 20 cm Vigreux column having Raschig rings (5×5 mm). Attached to the separating column was a column head having reflux regulator and Liebig condenser, and it was possible to operate it in all experiments without deposits of polymer.

The individual reactions were carried out by the following general working procedure: 2-hydroxyethylethyleneurea (HEEH, 130 g, 1.0 mol) was melted and blanketed with the appropriate amount of methyl methacrylate (MMA) (5.0 mol, 560 g). In the course of heating to internal temperature 100° C., the catalyst (0.8 mol % based on the urea) was added. The resulting azeotrope of methyl methacrylate (MMA) and methanol was distilled off at a reflux ratio of 2:1 (65° C.). At regular intervals, samples of distillate and bottoms were taken and analyzed. After the end of the evolution of methanol, operation was continued with a reflux ratio of 10:1 until six hours of experimental duration had been attained. The distillation was then switched off and the bottoms analyzed by gas chromatography for the 2-(2-oxoimidazolidin-1-yl)ethyl methacrylate product and secondary components formed (in total). The secondary components detected include N-[2-(2-oxooxazolidin-3-yl)ethyl]methacrylamide, N-{2-[3-(meth-acryloyl)-2-oxoimidazolidin-1-yl]ethyl}methacrylamide, 2-methyl-3-{3-[2-(methacryloylamino)ethyl]-2-oxoimidazolidin-1-yl}propionic acid and 2-methyl-3-[2-(2-oxoimidazolidin-1-yl)ethoxy]propionic acid.

Example 1

Potassium Phosphate

| Catalyst (mol %) | MMA [area %] | HEEH [area %] | Product [area %] | Dimethacrylate [area %] |
|---|---|---|---|---|
| Potassium phosphate (1.5) | 79.05 | 2.24 | 16.38 | 0.31 |
| Potassium phosphate (1.0) | 77.55 | 2.34 | 17.93 | 0.32 |
| Potassium phosphate (0.5) | 73.55 | 2.42 | 20.21 | 0.57 |

Example 2

Potassium Carbonate

| Catalyst (mol %) | MMA [area %] | HEEH [area %] | Product [area %] | Dimethacrylate [area %] |
|---|---|---|---|---|
| Potassium carbonate (0.2) | 78.65 | 1.38 | 16.16 | 0.48 |

Comparative Example 1

Dibutyltin Oxide (DBTO)

| Catalyst (mol %) | MMA [area %] | HEEH [area %] | Product [area %] | Dimethacrylate [area %] |
|---|---|---|---|---|
| DBTO (0.8) | 71.21 | 7.2 | 20.13 | 1.07 |

Comparative Example 2

Potassium Methoxide

| Catalyst | MMA [area %] | HEEH [area %] | Product [area %] | Dimethacrylate [area %] |
|---|---|---|---|---|
| Potassium methoxide (1 mol %) | 79.17 | 8.24 | 9.97 | 0.11 |

The comparison of the experiments shows clearly that potassium phosphate is superior as a catalyst to the existing systems. The esterification proceeds with high selectivity and high conversion at at least doubled space-time yield and low content of crosslinker. On cooling, the catalyst precipitates out in the form of readily filterable crystals and a washing step becomes unnecessary.

Example 3

Enzyme Catalysis

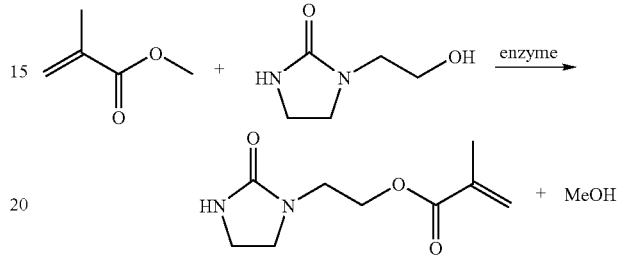

10 mmol of 2-hydroxyethylethyleneurea (HEEH, 1.3 g), 100 or 400 mmol of methyl methacrylate, 2.0 g of molecular sieve (5 Å) and 65-260 mg of Novozyme® 435 (immobilized lipase from *Candida antartica* B, from Novozymes) were agitated in a screwed-lid bottle at 40° C. for 72 h. Colorless solutions were obtained. To prepare the analyses, a homogeneous sample was prepared by dissolving any precipitates by adding 10 ml of 1,4-dioxane. The conversion of HEEH to the methacrylate was determined by gas chromatography by means of the above GC method.

Reactions with 100 mmol of MMA

| Amount of enzyme used | HEEH [area %] | Product [area %] | Σ secondary comp. [area %] | Conversion [%] |
|---|---|---|---|---|
| 130 mg | 46.1 | 52.9 | 1.0 | 53 |
| 260 mg | 33.3 | 65.8 | 0.8 | 66 |

Reactions with 400 mmol of MMA

| Amount of enzyme used | HEEH [area %] | Product [area %] | Σ secondary comp. [area %] | Conversion [%] |
|---|---|---|---|---|
| 65 mg | 41.7 | 57.1 | 0.8 | 58 |
| 130 mg | 43.4 | 55.7 | 0.7 | 56 |
| 260 mg | 13.2 | 86.1 | 0.6 | 87 |

What is claimed is:

1. A process for preparing (meth)acrylates of N-hydroxyalkylated amides, in which cyclic N-hydroxyalkylated amides (C)

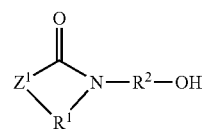

where

Z¹ is oxygen, sulfur, or unsubstituted or substituted phosphorus, $R^1$ and $R^2$ are each independently $C_2$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —$[X_i]_k$—H, $R^3$ is hydrogen, $C_1$-$C_{18}$-alkyl, or $C_2$-$C_{18}$-alkyl, $C_2$-$C_{18}$-alkenyl, $C_6$-$C_{12}$-aryl, $C_5$-$C_{12}$-cycloalkyl which are each optionally interrupted by one or more oxygen and/or sulfur atoms and/or one or more substituted or unsubstituted imino groups, or a five- to six-membered heterocycle having oxygen, nitrogen and/or sulfur atoms, where the radicals mentioned may each be substituted by aryl, alkyl, aryloxy, alkyloxy, heteroatoms and/or heterocycles, k is a number from 1 to 50 and $X_i$, for each i=1 to k may independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and —CHPh-$CH_2$—O— where Ph is phenyl and Vin is vinyl, are esterified with (meth)acrylic acid or transesterified with at least one (meth)acrylic ester (D) in the presence of at least one heterogeneous catalyst selected from the group consisting of inorganic salts (S) and enzymes (E), wherein the inorganic salt (S) has at least one cation, with the proviso that the at least one cation is not lithium; and at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($R^6$—COO$^-$), where $R^6$ is $C_1$-$C_{18}$-alkyl, or $C_2$-$C_{18}$-alkyl or $C_6$-$C_{12}$-aryl which are each optionally interrupted by one or more oxygen and/or sulfur atoms and/or one or more substituted or unsubstituted imino groups.

2. The process according to claim 1, wherein the at least one inorganic salt (S) has a $pK_B$ of not more than 7.0 and not less than 1.0, and a solubility in the reaction medium at 25° C. of not more than 1 g/l.

3. The process according to claim 1, wherein the inorganic salt has at least one cation selected from the group consisting of alkali metals, alkaline earth metals, ammonium, cerium, iron, manganese, chromium, molybdenum, cobalt, nickel and zinc, with the proviso that the at least one cation is not lithium.

4. The process according to claim 1, wherein the inorganic salt is selected from the group consisting of $K_3PO_4$, $Na_3PO_4$, $K_2CO_3$ and $Na_2CO_3$ and hydrates thereof.

5. The process according to claim 1, wherein the enzyme is selected from the group consisting of esterases (E.C.3.1.-.-), lipases (E.C.3.1.1.3), glycosylases (E.C. 3.2.-.-) and proteases (E.C.3.4.-.-).

6. The process according to claim 5, wherein the enzyme is selected from the group consisting of Novozyme® 435 (lipase from *Candida antarctica* B), lipase from *Alcaligenes* sp., *Aspergillus* sp., *Mucor* sp., *Penicilium* sp., *Geotricum* sp., *Rhizopus* sp., *Burkholderia* sp., *Candida* sp., *Pseudomonas* sp., *Thermomyces* sp. or porcine pancreas.

7. The process according to claim 1, wherein the reaction is carried out in such a way that the product (C) is obtained on completion of the reaction as an about 10-80% by weight solution in the (meth)acrylic ester used as the reactant.

8. A process for preparing (meth)acrylates of N-hydroxyalkylated amides, in which cyclic N-hydroxyalkylated amides (C)

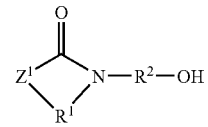

where $Z^1$ is N—$R^3$, $R^1$ and $R^2$ are each independently $C_2$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —$[X_i]_k$—H, $R^3$ is $C_1$-$C_{18}$-alkyl, $C_2$-$C_{18}$-alkyl, $C_2$-$C_{18}$-alkenyl, $C_6$-$C_{12}$-aryl, $C_5$-$C_{12}$-cycloalkyl which are each optionally interrupted by one or more oxygen and/or sulfur atoms and/or one or more substituted or unsubstituted imino groups, or a five- to six-membered heterocycle having oxygen, nitrogen and/or sulfur atoms, where the radicals mentioned may each be substituted by aryl, alkyl, aryloxy, alkyloxy, heteroatoms and/or heterocycles, k is a number from 1 to 50 and $X_i$, for each i=1 to k may independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and —CHPh-$CH_2$—O— where Ph is phenyl and Vin is vinyl, are esterified with (meth)acrylic acid or transesterified with at least one (meth)acrylic ester (D) in the presence of at least one heterogeneous catalyst selected from the group consisting of inorganic salts (S) and enzymes (E), wherein the inorganic salt (S) has at least one cation, with the proviso that the at least one cation is not lithium; and at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($R^6$—COO$^-$), where $R^6$ is $C_1$-$C_{18}$-alkyl, or $C_2$-$C_{18}$-alkyl or $C_6$-$C_{12}$-aryl which are each optionally interrupted by one or more oxygen and/or sulfur atoms and/or one or more substituted or unsubstituted imino groups.

9. A process for preparing (meth)acrylates of N-hydroxyalkylated amides, in which cyclic N-hydroxyalkylated amides (C)

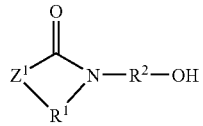

where $Z^1$ is $N-R^3$, $R^1$ is $C_3$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, $R^2$ is $C_2$-$C_{20}$-alkylene, $C_5$-$C_{12}$-cycloalkylene, $C_6$-$C_{12}$-arylene, or $C_2$-$C_{20}$-alkylene interrupted by one or more oxygen and/or sulfur atoms and/or one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, where the radicals mentioned may each be substituted by aryl, alkyl, aryloxy, alkyloxy, heteroatoms and/or heterocycles, or $R^2$—OH is a group of the formula —[$X_i$]$_k$—H, $R^3$ is hydrogen, k is a number from 1 to 50 and $X_i$, for each i=1 to k may independently be selected from the group of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh-O— and —CHPh-$CH_2$—O— where Ph is phenyl and Vin is vinyl, are esterified with (meth)acrylic acid or transesterified with at least one (meth)acrylic ester (D) in the presence of at least one heterogeneous catalyst selected from the group consisting of inorganic salts (S) and enzymes (E), wherein the inorganic salt (S) has at least one cation, with the proviso that the at least one cation is not lithium; and at least one anion selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($R^6$—COO$^-$), where $R^6$ is $C_1$-$C_{18}$-alkyl, or $C_2$-$C_{18}$-alkyl or $C_6$-$C_{12}$-aryl which are each optionally interrupted by one or more oxygen and/or sulfur atoms and/or one or more substituted or unsubstituted imino groups.

* * * * *

UNITED STATES PATENT AND TRADEMARK OFFICE
CERTIFICATE OF CORRECTION

| | | |
|---|---|---|
| PATENT NO. | : 7,816,485 B2 | Page 1 of 1 |
| APPLICATION NO. | : 11/169763 | |
| DATED | : October 19, 2010 | |
| INVENTOR(S) | : Frank Hoefer et al. | |

It is certified that error appears in the above-identified patent and that said Letters Patent is hereby corrected as shown below:

On the title page, Item (75), the first inventor's name is incorrect. Item (75) should read:

-- (75)  Inventors:  Frank Hoefer, Bad Duerkheim (DE);
   Dietmar Haering, Schriesheim (DE) --

Signed and Sealed this
First Day of February, 2011

David J. Kappos
*Director of the United States Patent and Trademark Office*